United States Patent
Healy et al.

(12)

(10) Patent No.: US 7,222,373 B2
(45) Date of Patent: May 29, 2007

(54) EAR WARMER HAVING A MEMBRANE FORMING A RECEPTACLE

(75) Inventors: Teresa S. Healy, Baltimore, MD (US); Alan S. Tipp, Ellicott City, MD (US)

(73) Assignee: 180s, Inc., Baltimore, MD (US)

( * ) Notice: Subject to any disclaimer, the term of this patent is extended or adjusted under 35 U.S.C. 154(b) by 232 days.

(21) Appl. No.: 10/638,554

(22) Filed: Aug. 12, 2003

(65) Prior Publication Data

US 2005/0034217 A1    Feb. 17, 2005

(51) Int. Cl.
*A42B 1/06*    (2006.01)
(52) U.S. Cl. .......................................................... 2/209
(58) Field of Classification Search ................. 2/209; 128/857
See application file for complete search history.

(56) References Cited

U.S. PATENT DOCUMENTS

| 138,894 | A | 5/1873 | Isidor |
|---|---|---|---|
| 139,831 | A | 6/1873 | Stone |
| 183,359 | A | 10/1876 | Abbott |
| 188,292 | A | 3/1877 | Greenwood |
| 360,985 | A | 4/1887 | Basch |
| 365,061 | A | 6/1887 | Friedman |
| 548,738 | A | 10/1895 | Ballard |
| 804,731 | A | 11/1905 | Keller |
| 836,087 | A | 11/1906 | Callahan |
| 869,741 | A | 10/1907 | Seitzman |
| 932,487 | A | 8/1909 | Melio |
| 953,623 | A | 3/1910 | Keller |
| 1,167,368 | A | 4/1916 | Adams-Randall |
| 1,179,473 | A | 4/1916 | Taylor |
| 1,274,842 | A | 8/1918 | Basch |
| 1,326,875 | A | 12/1919 | Miller |
| 1,398,958 | A | 12/1921 | Basch |
| 1,567,105 | A | 12/1925 | Bohlman |
| 1,577,183 | A | 3/1926 | Dowiarz |
| 1,628,483 | A | 5/1927 | Wiegand et al. |
| 1,988,880 | A | 1/1935 | Strouse |
| 2,070,216 | A | 2/1937 | Rosenberg |
| 2,216,954 | A | 10/1940 | McDonough |
| 2,246,031 | A | 6/1941 | Baritz et al. |
| 2,314,782 | A | 3/1943 | Goretsky |

(Continued)

FOREIGN PATENT DOCUMENTS

CA    2180036    1/1997

(Continued)

OTHER PUBLICATIONS

U.S. Appl. No. 10/335,930, filed Jan. 3, 2003, Le Gette et al.

(Continued)

*Primary Examiner*—Katherine Moran
(74) *Attorney, Agent, or Firm*—Edell, Shapiro & Finnan, LLC

(57) ABSTRACT

An ear warmer includes a cover and a membrane coupled to the cover. The membrane is disposable in a deployed configuration and in a retracted configuration. When the membrane is disposed in its deployed configuration, the membrane and the cover form a receptacle that is configured to receive an ear or a portion of an ear of a user when the ear warmer is worn by the user.

26 Claims, 14 Drawing Sheets

U.S. PATENT DOCUMENTS

| | | |
|---|---|---|
| 2,333,392 A | 11/1943 | Rosenzweig |
| 2,378,398 A | 6/1945 | Fiedler |
| 2,405,326 A | 8/1946 | Plotsky |
| 2,420,245 A | 5/1947 | Hurst |
| 2,437,049 A | 3/1948 | Salisbury et al. |
| 2,532,852 A | 12/1950 | Oaks |
| 2,582,907 A | 1/1952 | Kaufmann |
| 2,586,644 A | 2/1952 | Gilbert |
| 2,615,169 A | 10/1952 | Maxant |
| 2,651,046 A | 9/1953 | Berg |
| 2,671,221 A | 3/1954 | Triplett |
| 2,717,930 A | 9/1955 | Hintz |
| 2,776,436 A | 1/1957 | Berg |
| 2,858,544 A | 11/1958 | Roth |
| 2,899,683 A | 8/1959 | Wadsworth et al. |
| 2,946,860 A | 7/1960 | Jansen et al. |
| 3,087,028 A | 4/1963 | Bonnin |
| 3,104,398 A | 9/1963 | Palmaer |
| 3,112,493 A | 12/1963 | Greenberg |
| 3,119,119 A | 1/1964 | Millinger et al. |
| 3,156,923 A | 11/1964 | Timm |
| 3,249,949 A | 5/1966 | Rosenberg et al. |
| 3,308,480 A | 3/1967 | Elder |
| 3,311,713 A | 3/1967 | Knuebel |
| 3,440,663 A | 4/1969 | Beguin |
| 3,447,160 A | 6/1969 | Teder |
| 3,509,580 A | 5/1970 | Rubenstein et al. |
| 3,721,993 A | 3/1973 | Lonnstedt |
| 3,728,741 A | 4/1973 | Lepor |
| 3,787,899 A | 1/1974 | Krawagna |
| 3,841,325 A | 10/1974 | Pickard |
| 3,944,018 A | 3/1976 | Satory |
| 4,065,176 A | 12/1977 | Fontana |
| 4,277,847 A | 7/1981 | Florio |
| 4,349,081 A | 9/1982 | Pepple |
| 4,391,000 A | 7/1983 | Lonnstedt |
| 4,404,434 A | 9/1983 | Pelt et al. |
| 4,409,442 A | 10/1983 | Kamimura |
| 4,445,005 A | 4/1984 | Furuhashi |
| 4,455,457 A | 6/1984 | Akira |
| 4,463,223 A | 7/1984 | Yamanoi et al. |
| 4,471,496 A | 9/1984 | Gardner, Jr. et al. |
| 4,486,903 A | 12/1984 | Krystal |
| 4,499,593 A | 2/1985 | Antle |
| 4,516,274 A | 5/1985 | Buckland |
| 4,542,803 A | 9/1985 | Houng |
| 4,546,215 A | 10/1985 | Ferraro |
| 4,571,746 A | 2/1986 | Görike |
| 4,615,185 A | 10/1986 | Bollinger |
| 4,633,530 A | 1/1987 | Satterfield |
| 4,654,898 A | 4/1987 | Ishikawa |
| 4,660,229 A | 4/1987 | Harris |
| 4,662,590 A | 5/1987 | Hungerford, Jr. |
| 4,669,129 A | 6/1987 | Chance |
| 4,670,911 A | 6/1987 | Dunford |
| 4,682,374 A | 7/1987 | Geiser |
| 4,713,843 A | 12/1987 | Duncan |
| 4,727,599 A | 2/1988 | Rappaport et al. |
| 4,747,145 A | 5/1988 | Wiegel |
| 4,776,042 A | 10/1988 | Hanson et al. |
| 4,776,044 A | 10/1988 | Makins |
| 4,783,822 A | 11/1988 | Toole et al. |
| 4,791,684 A | 12/1988 | Schwartz |
| 4,796,307 A | 1/1989 | Vantine |
| 4,802,245 A | 2/1989 | Miano |
| D301,477 S | 6/1989 | Storyk |
| 4,858,248 A | 8/1989 | Goldsmith et al. |
| 4,864,619 A | 9/1989 | Spates |
| 4,872,219 A | 10/1989 | Duncan |
| 4,907,266 A | 3/1990 | Chen |
| 4,918,757 A | 4/1990 | Janssen et al. |
| 4,982,451 A | 1/1991 | Graham |
| 5,003,589 A | 3/1991 | Chen |
| 5,033,094 A | 7/1991 | Hung |
| 5,038,412 A | 8/1991 | Cionni |
| 5,046,192 A | 9/1991 | Ryder |
| 5,052,194 A | 10/1991 | Jarus |
| 5,086,789 A | 2/1992 | Tichy |
| 5,117,464 A | 5/1992 | Jones et al. |
| 5,117,465 A | 5/1992 | MacDonald |
| 5,164,987 A | 11/1992 | Raven |
| 5,201,856 A | 4/1993 | Edwards |
| 5,257,420 A | 11/1993 | Byrne, Jr. |
| 5,303,426 A | 4/1994 | Jones |
| 5,327,178 A | 7/1994 | McManigal |
| 5,339,467 A | 8/1994 | Brinkley |
| 5,357,585 A | 10/1994 | Kumar |
| 5,509,146 A | 4/1996 | Bryerton, Sr. |
| 5,528,774 A | 6/1996 | Sanders |
| 5,545,859 A | 8/1996 | Ullrich |
| 5,551,089 A | 9/1996 | Whidden |
| 5,551,090 A | 9/1996 | Thompson |
| D375,825 S | 11/1996 | Whidden |
| 5,617,589 A | 4/1997 | Lacore et al. |
| 5,625,903 A | 5/1997 | Schultz et al. |
| 5,673,438 A | 10/1997 | Lambert |
| 5,691,515 A | 11/1997 | Landis |
| D390,564 S | 2/1998 | Savona |
| 5,718,001 A | 2/1998 | Wright |
| 5,724,119 A | 3/1998 | Leight |
| 5,749,099 A | 5/1998 | Voorhees |
| 5,793,878 A | 8/1998 | Chang |
| 5,821,468 A | 10/1998 | Urella et al. |
| 5,835,609 A * | 11/1998 | LeGette et al. ............ 381/385 |
| 5,860,166 A | 1/1999 | Ritts |
| 5,887,286 A | 3/1999 | Waldron |
| 5,898,945 A | 5/1999 | Weiser |
| 5,943,703 A | 8/1999 | Avila, Jr. |
| 5,953,434 A | 9/1999 | Boyden |
| 6,016,574 A | 1/2000 | Chen |
| 6,029,282 A | 2/2000 | Buschman |
| 6,055,672 A | 5/2000 | Natvig |
| 6,065,157 A * | 5/2000 | Felman .................... 2/209 |
| 6,104,824 A | 8/2000 | Ito |
| 6,148,446 A | 11/2000 | Leight |
| 6,332,223 B1 * | 12/2001 | Le Gette et al. ............ 2/209 |
| 6,377,697 B1 | 4/2002 | Cheng |
| 6,499,146 B2 | 12/2002 | Bavetta et al. |
| 6,502,247 B2 | 1/2003 | Le Gette et al. |
| 6,502,248 B2 * | 1/2003 | LeGette et al. ............ 2/209 |
| D473,539 S | 4/2003 | O'Leary |
| 6,580,800 B1 * | 6/2003 | Yamasaki et al. .......... 381/379 |
| 6,735,784 B2 * | 5/2004 | Isom et al. ................. 2/209 |
| 6,744,901 B2 | 6/2004 | Ito et al. |
| 2003/0088905 A1 | 5/2003 | Bavetta et al. |
| 2004/0005071 A1 | 1/2004 | Siskin et al. |
| 2004/0187192 A1 | 9/2004 | Isom et al. |
| 2005/0034216 A1 | 2/2005 | Le Gette et al. |
| 2005/0034218 A1 | 2/2005 | Le Gette et al. |
| 2005/0036643 A1 | 2/2005 | Le Gette et al. |
| 2005/0241047 A1 | 11/2005 | Bavetta et al. |
| 2005/0246815 A1 | 11/2005 | Le Gette et al. |

FOREIGN PATENT DOCUMENTS

| | | |
|---|---|---|
| CH | 294003 | 1/1954 |
| CN | 2291138 | 9/1998 |
| DE | 2516709 A1 | 10/1976 |
| DE | 3231218 A1 | 2/1984 |
| DE | 4422767 A1 | 1/1996 |
| DE | 29800973 U1 | 4/1998 |
| DE | 29812652 U1 | 3/1999 |
| EP | 0745364 A2 | 4/1996 |
| FR | 1 353 524 | 1/1964 |

| | | |
|---|---|---|
| FR | 2538204 A1 | 12/1982 |
| FR | 2 532 838 A1 | 3/1984 |
| FR | 2 536 253 A | 5/1984 |
| GB | 1327614 | 8/1973 |
| GB | 2062478 A | 5/1981 |
| GB | 2320885 A | 7/1998 |
| GB | 2339642 A | 2/2000 |
| JP | 47-19024 | 11/1972 |
| JP | 48-75626 | 9/1973 |
| JP | 53-143627 | 11/1978 |
| JP | 57-11884 | 1/1982 |
| JP | 57-205216 | 12/1982 |
| JP | 58-15618 | 1/1983 |
| JP | 58-138484 | 9/1983 |
| JP | 59-129815 | 8/1984 |
| JP | 60-29141 | 2/1985 |
| JP | 60-244188 A | 12/1985 |
| JP | 62-21016 | 2/1987 |
| JP | 63-20232 | 6/1988 |
| JP | 63-21972 | 8/1989 |
| JP | 6-41720 | 6/1994 |
| JP | 6-351090 A | 12/1994 |
| JP | 10-079994 | 3/1998 |
| JP | 10-85251 | 4/1998 |
| JP | 11-229223 | 8/1999 |
| JP | 10257581 | 8/2000 |
| JP | 2002-11036 A | 1/2002 |
| KR | 20-0226271 | 6/2001 |
| KR | 20-0314976 | 6/2003 |
| KR | 30-0336877 | 11/2003 |
| KR | 20-2004-0007721 | 3/2004 |
| KR | 20-2004-0007722 | 3/2004 |
| WO | WO 92/17079 | 10/1992 |
| WO | WO 94/09734 | 5/1994 |
| WO | WO 97/48296 | 12/1997 |
| WO | WO 98/07062 | 2/1998 |
| WO | WO 98/31314 | 7/1998 |
| WO | WO 01/76402 A1 | 10/2001 |
| WO | WO 02/083044 | 10/2002 |
| WO | WO 03/086124 | 10/2003 |

OTHER PUBLICATIONS 1999-2000 Catalog , "Accessory Goods," Nitty Company, Ltd., 4 pgs.

Advertisement: The "PODZ" ear warming eye glass retainer, Shred Alert Products of Hood River, Oregon, 5 pgs.

Chicago Tribune article entitled "Winter From Head to Toe Lend an Ear to the Tale of This Intrepid Inventor," by Sid Moody, Feb. 16, 1988, 4 pgs.

"History of the United States Patent Office—The Patent Office Pony—A History of the Early Patent Office", by Kenneth W. Dobyns, 1994, [Introductory Material—3 pgs.; Chapter 29—4 pgs.; and Sources and Annotations—40 pgs.].

Design U.S. Appl. No. 29/201,175 entitled "Ear Warmer Having an External Frame", filed on Mar. 12, 2004.

Design U.S. Appl. No. 29/201,219 entitled "Ear Warmer Having an External Frame", filed on Mar. 12, 2004.

* cited by examiner

EAR WARMER HAVING A MEMBRANE FORMING A RECEPTACLE

CROSS-REFERENCES TO OTHER APPLICATIONS

This application is related to co-pending U.S. patent application entitled "Ear Warmer Having an External Frame," application Ser. No. 10/638,476, filed the same day; and co-pending U.S. patent application entitled "Ear Warmer With a Speaker System," application Ser. No. 10/638,553, filed the same day; the disclosures of each are incorporated herein by reference.

BACKGROUND OF THE INVENTION

This invention relates generally to ear warmers, and in particular to ear warmers that are configured to extend around the back of a user's head.

Conventional ear warmers extend over the top of a user's head. To retain such a conventional ear warmer in place on the user, a top of the user's head provides support to the ear warmer. Ear warmers that are configured to extend around the back of a user's head, however, are not supported by the head of the user. Therefore, ear warmers that are configured to extend around the back of a user's head may have a tendency, especially during extreme physical activity, such as running or jogging, to slip or slide away from a particular placement on the user's head.

A need, therefore, exists for an ear warmer that is configured to extend around the back of a user's head that, when placed on the user, resists movement of ear warmer with respect to the user.

SUMMARY OF THE INVENTION

An ear warmer includes a cover and a membrane coupled to the cover. The membrane is disposable in a deployed configuration and in a retracted configuration. When the membrane is disposed in its deployed configuration, the membrane and the cover form a receptacle that is configured to receive an ear or a portion of an ear of a user when the ear warmer is worn by the user.

DETAILED DESCRIPTION

An ear warmer includes a cover and a membrane coupled to the cover. The membrane is disposable in a deployed configuration and in a retracted configuration. When the membrane is disposed in its deployed configuration, the membrane and the cover form a receptacle that is configured to receive an ear or a portion of an ear of a user when the ear warmer is worn by the user.

Figure 1:
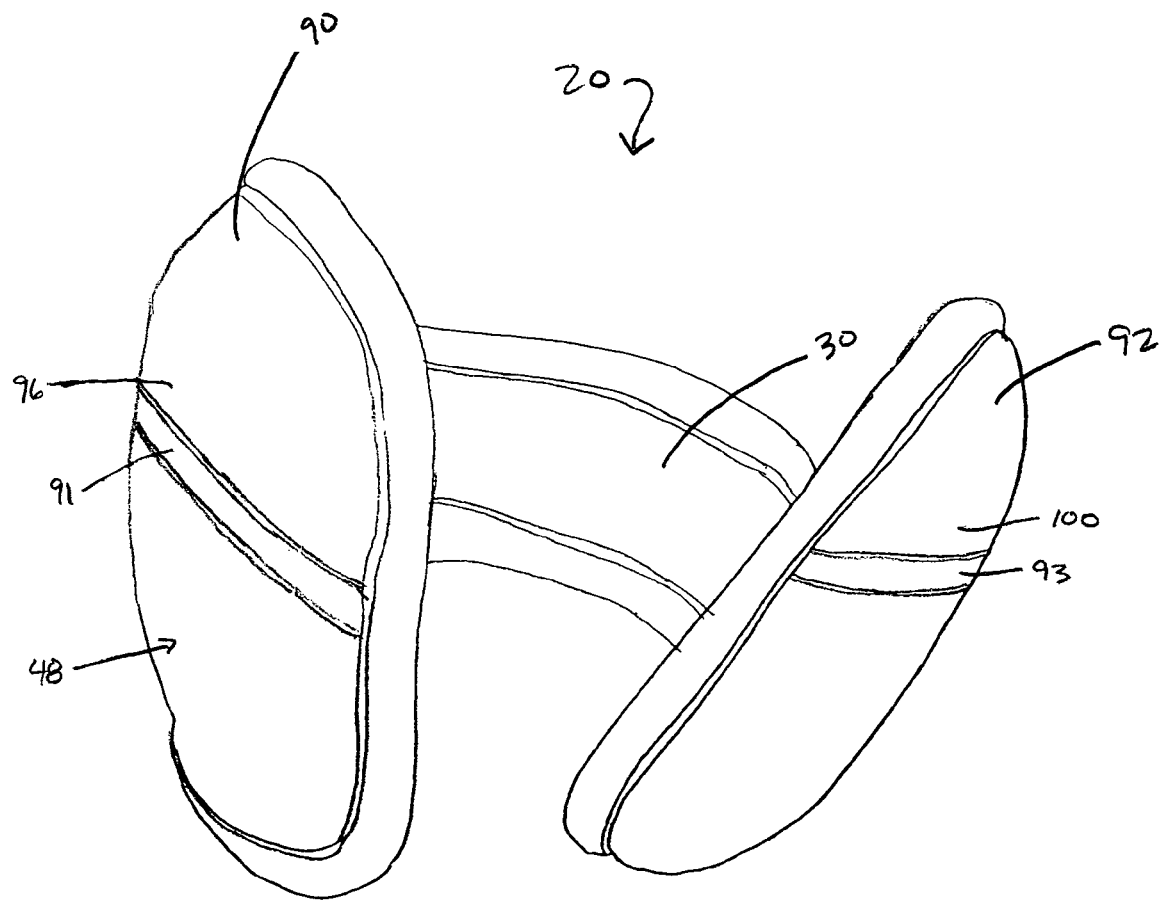
FIG. 1 is a perspective view of an ear warmer according to an embodiment of the invention disposed in one configuration.

An ear warmer 20 according to an embodiment of the invention is illustrated in FIGS. 1–8. In the illustrated embodiment, the ear warmer 20 includes a cover 30, two membranes 90 and 92, and a frame 80. FIG. 1 illustrates the ear warmer 20 in a first configuration.

Figure 2:
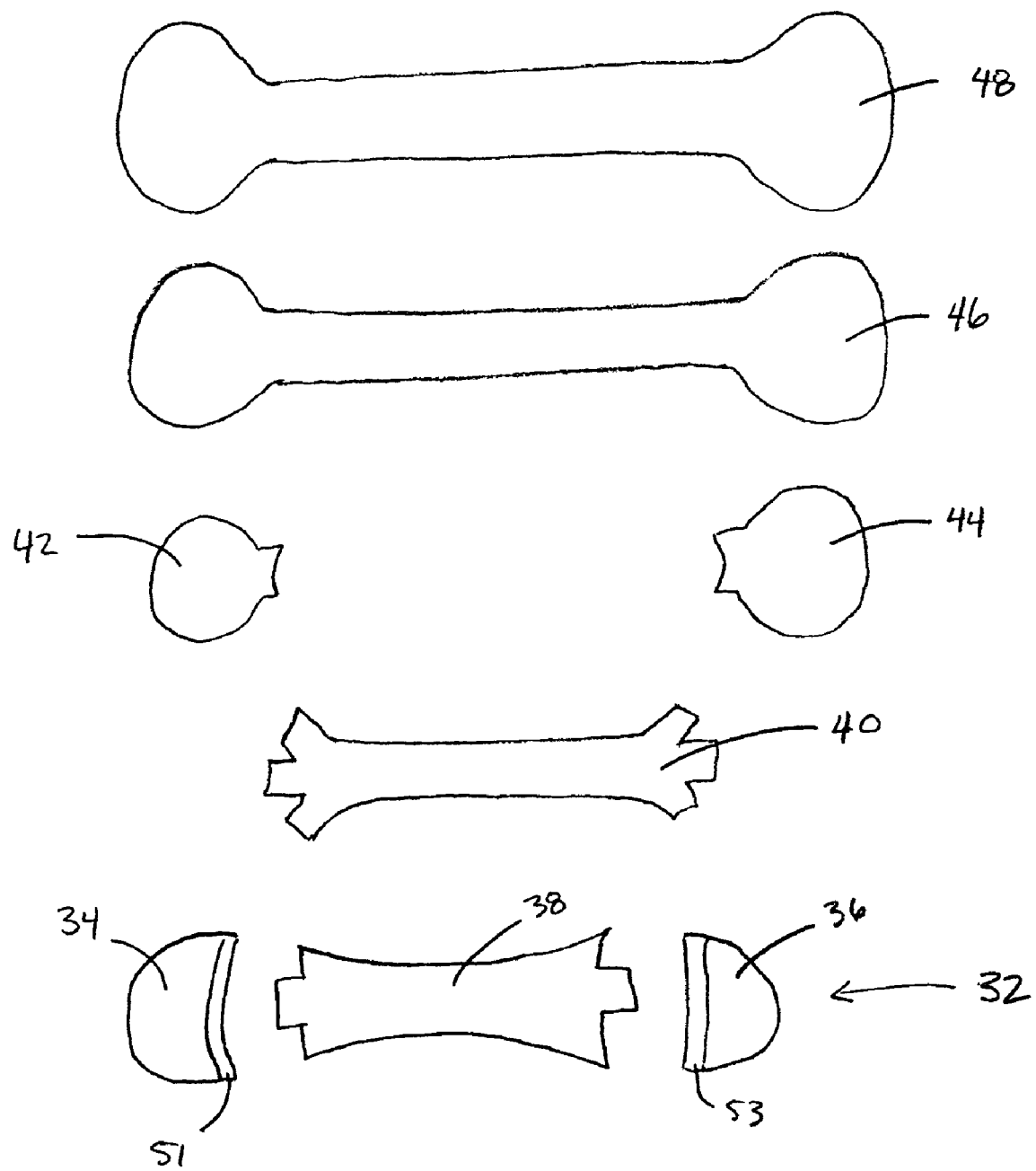
FIG. 2 is an exploded assembly view of members of a cover of an ear warmer according to an embodiment of the invention.
Figure 3:
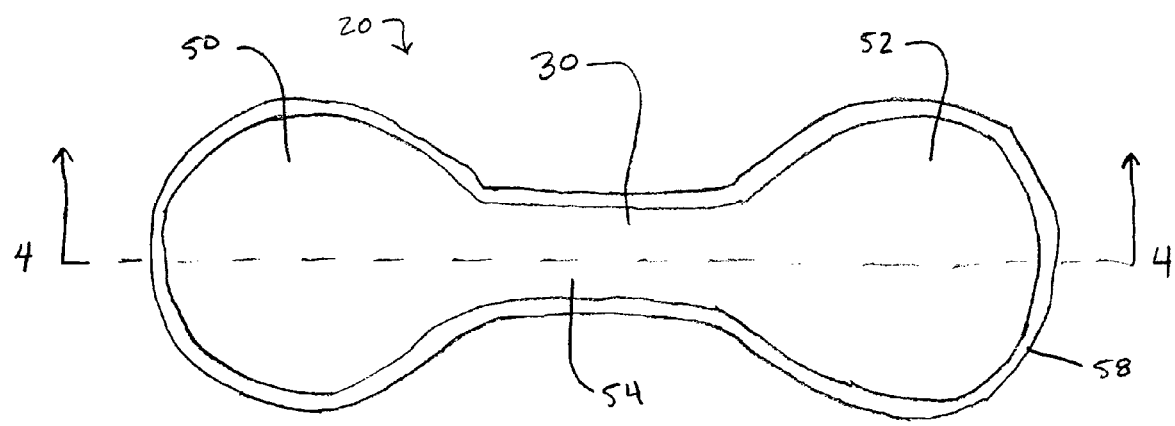
FIG. 3 is a top view of the ear warmer illustrated in FIG. 1 in an extended planar configuration.

An example of an embodiment of a cover is illustrated in FIGS. 2–4. In this embodiment, the cover 30 of the ear warmer 20 has ear portions 50 and 52 and a middle portion 54 as illustrated in FIG. 3. As illustrated in FIG. 2, the cover 30 includes an inner member or assembly 32 and an outer member 48. The inner member 32 is configured to be disposed adjacent a user's head when the ear warmer 20 is worn by the user. The inner member 32 can be a single member or an assembly of members as illustrated in FIG. 2.

The outer member 48 is disposed opposite the inner member 32 and is configured to be disposed apart from a user's head when the ear warmer 20 is worn by the user. In other words, the outer member 48 is configured to be in a non-contact position with respect to the user's head when the ear warmer 20 is worn by the user. An interior region 56 is defined by the inner member 32 and the outer member 48 (see FIG. 4). The frame 80 and other items may be disposed within the interior region 56 defined by the inner member 32 and the outer member 48. In one embodiment, the inner member 32 and the outer member 48 are unitary or monolithically formed.

In this embodiment, additional members, including a heat-retaining member 46, ear pads 44 and 42, and a neckpiece 40 are disposed within the interior region 56 defined by the inner member 32 and the outer member 48. In other embodiments, some or all of the additional members are not necessarily present. In further embodiments, speakers are disposed within the interior region defined by the inner member and the outer member.

In this embodiment, the outer member 48 of the cover 30 is made of a material that functions as a barrier between the ambient conditions and the interior region 56 of the cover 30. Specifically, the outer member 48 prevents moisture and air from entering the interior region 56 of the cover 30. In one embodiment, the outer member 48 can also function to wick away moisture from the interior region 56. In one embodiment, the outer member is made of Power-Dry® material, available from Malden Mills. In alternative embodiments, the outer member is made of other types of material and can perform any or all of the previously described different functions.

The heat-retaining member 46 is configured to retain the heat displaced by a user wearing the ear warmer 20. Additionally, the heat-retaining member 46 is configured to provide cushioning or padding to the ear warmer 20. In this embodiment, the heat-retaining member 46 is a fleece material. In alternative embodiments, however, the heat-retaining member is made of another material that retains heat. In other embodiments, the heat-retaining member can be replaced with a member made of a material that does not retain heat, rather; the heat-retaining member is made of a material that provides cushioning, padding, or support to the ear warmer or to a user.

The ear pads 42 and 44 function as an insulation layer for the ear warmer 20. In one embodiment, the ear pads 42 and 44 are made of a Thermolite® material, available from Dupont. In an alternative embodiment, the ear pads are made of a soft or elastic material or any other material that provides cushioning, padding, or support to the ear warmer or to a user.

The neckpiece 40 is configured to retain some of the heat displaced by a user wearing the ear warmer 20. Additionally, the neckpiece 40 is configured to provide cushioning or padding to the ear warmer 20. In this embodiment, the neckpiece 40 is made of a fleece material. In alternative embodiments, however, the neckpiece can be made of any type of material that provides comfort to a user.

In one embodiment, the inner member or assembly 32 includes ear portions 34 and 36 and a middle portion 38. As illustrated in FIG. 2, each of the ear portions 34 and 36 includes a binding or a piece of material 51 and 53, respectively, that covers an end of the respective ear portion. It is not necessary, however, that the ear portions 34 and 36 include bindings 51 and 53. Additionally, it is not necessary that the inner member or assembly include a middle portion.

In this embodiment, the inner member 32, including the ear portions 34 and 36 and the middle portion 38, is made of a hydrophobic material or a material that is rendered hydrophobic. The material of the ear portion 34 and 36 and the middle portion 38 of the inner member 32 wicks perspiration or other wetness away from a user's head. In one embodiment, the inner member 32 can be made of dri-release® material, available from United Knitting. In an alternative embodiment, the inner member is made of a different material, such as a fleece material or another type of material configured to provide comfort, such as temperature and/or moisture control, to the user. In another alternative embodiment, the portions of the inner member are not made of the same material. In a further embodiment, the inner member is made of a single piece of material.

Although the layers of the cover, including the outer member, the heat-retaining member, the ear pads, the neckpiece, and the inner member, have been described as being made of certain materials and providing certain functions, it is not necessary that all of the layers be present in the cover. Additionally, the different layers of the cover may provide different functions than those discussed above. In further embodiments, some or all of the layers of the cover are configured to stretch and mold to the shape of a user's ear. The layers, in such embodiments, enable the product to have a better friction fit due to more surface area being in contact with the user's ear. Additionally, in such embodiments, the layers of the cover provide added comfort, such as fit, temperature control, and moisture control, to the user.

A partial cross-sectional view of an ear portion of the cover of FIG. 3 is illustrated in FIG. 4. Referring to FIGS. 2 and 4, in one embodiment, the different layers of the cover 30 are stacked in a pile so the layers can be coupled together. For example, the neckpiece 40 (not illustrated in FIG. 4) is stacked on top of the inner member 32 (of which ear portion 34 is illustrated in FIG. 4), the ear pads 42 and 44 (ear pad 44 is not illustrated in FIG. 4) are stacked on the neckpiece 40 and the ear portions 34 and 36, the heat-retaining member 46 is stacked on top of the ear pads 42 and 44, and the outer member 48 is stacked on top of the heat-retaining member 46. As illustrated in FIGS. 3 and 4, a binding 58 is placed along the perimeter of the layers of the cover 30 such that the binding 58 encloses an end portion of the stack of layers of the cover, and the binding 58 is sewn therethrough. In particular, a seam is sewn though one portion of the binding 58, through the pile of layers, and through another portion of the binding 58. The binding 58 can be formed of one or more sections. The term "perimeter" is intended herein to include the perimeter or a portion offset from and proximate to the perimeter of a membrane, member or portion.

In an alternative embodiment, the layers of the cover are stacked in a pile and are sewn together without the binding being present. In a further alternative embodiment, the layers of the cover may be coupled via an interior seam. In other words, after sewing the layers together, the seam can be disposed within an interior region of the cover by turning the sewn cover inside out. One example of an interior seam is disclosed in U.S. Pat. No. 6,332,223 B1, the disclosure of which is incorporated herein by reference.

Referring to FIG. 1, the ear warmer 20 includes membranes 90 and 92 coupled to the cover 30. The membranes 90 and 92 are flexible members, such as fabric or mesh members. The membranes 90 and 92, however, need not be fabric or mesh members. The membranes 90 and 92 are coupled to the cover 30 and are configured to be disposed in several different configurations.

Figures 5A, 5B:
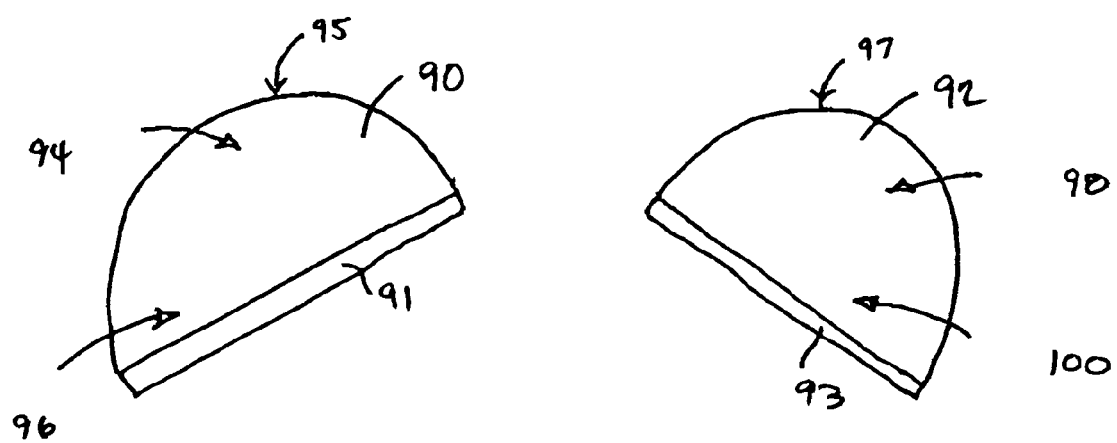
FIGS. 5A and 5B are side views of membranes according to another embodiment of the invention.

Referring to FIGS. 1, 5A and 5B, the membrane 90 includes a proximal portion 94 (the portion of the membrane 90 that is proximal to the coupling of the membrane 90 and the cover 30) and a distal portion 96 (the portion of the membrane 90 that is distal from the coupling of the membrane 90 and the cover 30). The proximal portion 94 can be referred to as a fixed portion, and the distal portion 96 can be referred to as a movable portion (see FIGS. 7 and 8). The membrane 92 includes a proximal portion 98 (the portion of the membrane 92 that is proximal to the coupling of the membrane 92 and the cover 30) and a distal portion 100 (the portion that is distal from the coupling of the membrane 92 and the cover 30).

In this embodiment, each of the membranes 90 and 92 includes a binding 91 and 93, respectively, coupled to a portion of the membranes 90 and 92 such as the distal portions 96 and 100, respectively. It is not necessary, however, that either or both of the membranes 90 and 92 include the bindings 91 and 93.

Figure 4A:
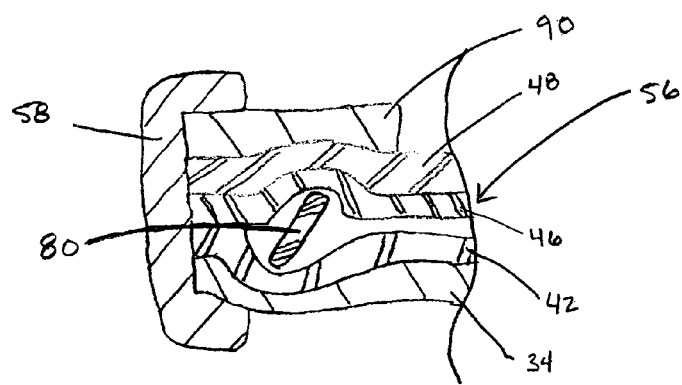
FIG. 4A is a partial cross-sectional view of the ear warmer illustrated in FIG. 1 taken along line 4—4 of FIG. 3.
Figure 4B:
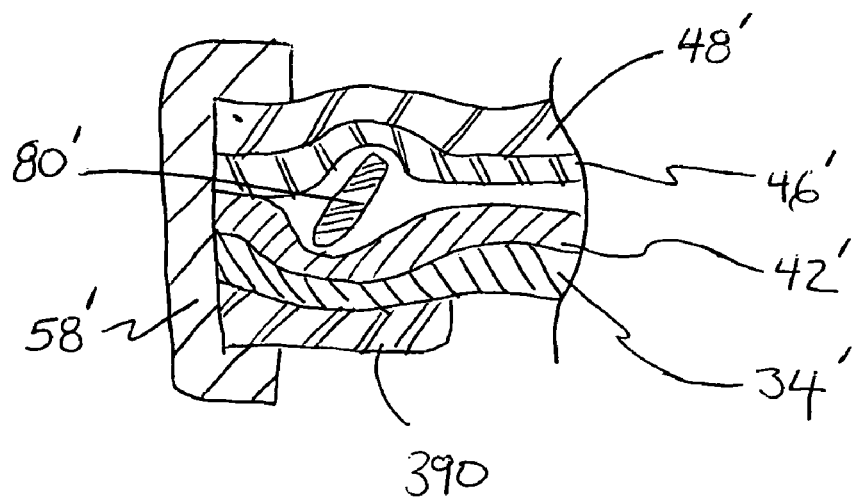
FIG. 4B is a partial cross-sectional view of an ear warmer illustrated according to an embodiment of the invention.
Figure 4C:
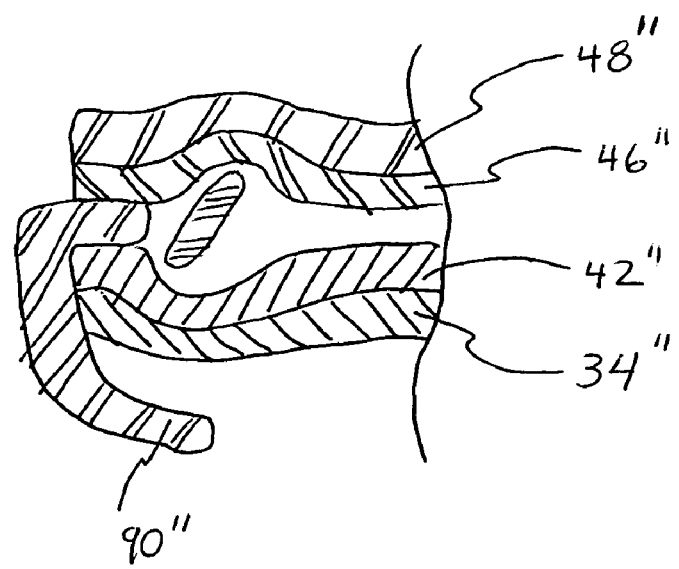
FIG. 4C is a partial cross-sectional view of an ear warmer illustrated according to an embodiment of the invention.

In one embodiment, a portion 95 of the membrane 90 is coupled to the outer member 48 of the cover 30 along a portion of a perimeter of the ear portion 50 of the cover 30. Similarly, a portion 97 of the membrane 92 is coupled to the outer member 48 of the cover 30 along a portion of a perimeter of the ear portion 52 of the cover 30. In alternative embodiments, however, the membranes 90 and 92 may be coupled to any other portion of the outer member 48 of the cover 30, to any portion of the inner member 32' of the cover (see FIG. 4B), between the inner member 32" and the outer member 48" (see FIG. 4C), or to any other portion of the cover 30. As illustrated in FIG. 4A, membrane 90 is sewn via a binding 58 to the outer member 48 of the cover 30. Membrane 92 is similarly sewn via a binding to the outer member 48 of the cover 30. In an alternative embodiment, the membranes 90 and 92 may be coupled to the outer member 48 via tacks, via an adhesive, such as glue, or via any other known coupling device or technique. In another embodiment, the membranes 90 and 92 are coupled to the cover 30 via an interior seam, as previously discussed.

As illustrated in FIG. 1, each of the membranes 90 and 92 may be disposed in a retracted configuration. In the retracted configurations, the distal portions 96 and 100 of the membranes 90 and 92, respectively, are disposed adjacent the outer member 48 of the cover 30. In these configurations, the membranes 90 and 92 are disposed not in contact with a user's head when the ear warmer 20 is worn by the user.

Figure 6:
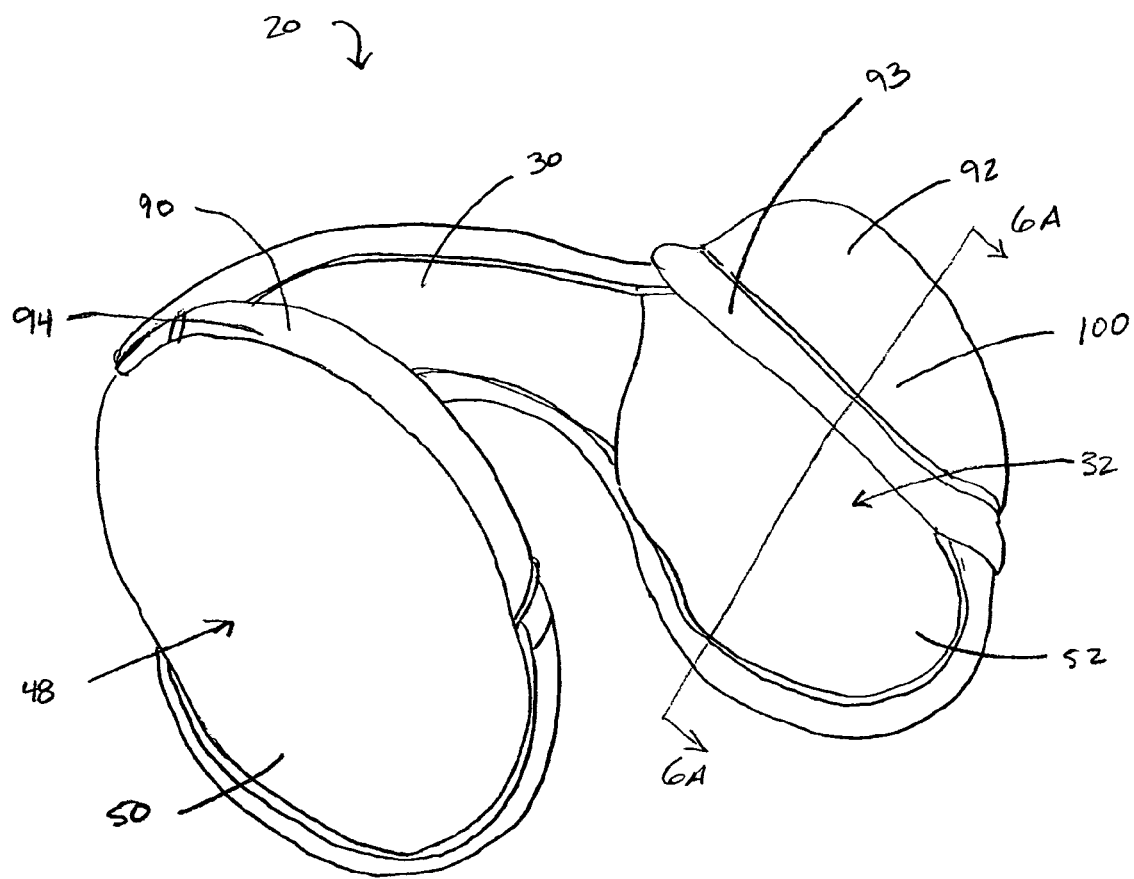
FIG. 6 is a perspective view of the ear warmer illustrated in FIG. 1 disposed in another configuration.

As illustrated in FIG. 6, each of the membranes 90 and 92 may be disposed in a deployed configuration. In the deployed configurations, the distal portions 96 and 100 of the membranes 90 and 92, respectively, are disposed adjacent the inner member 32 of the cover 30. In these configurations, the proximal portion 94 of the membrane 90 extends over a portion of a perimeter of the ear portion 50 of the cover 30. Similarly, the proximal portion 98 (not illustrated) of the membrane 92 extends over a portion of a perimeter of the ear portion 52 of the cover 30.

In the deployed configurations, the membranes 90 and 92 are disposed adjacent a user's head when the ear warmer 20 is worn by the user. The membrane 90 and inner member 32 of the cover 30 form a receptacle that is configured to receive an ear or a portion of an ear of a user. Similarly, the membrane 92 and the inner member 32 of the cover 30 form a receptacle that is configured to receive an ear or a portion of an ear of a user. Therefore, when the membranes 90 and 92 are in their deployed configurations, a user may place the ear warmer 20 on the head of the user and may insert an ear or a portion of an ear into each of the receptacles formed by the membranes and the inner member 32. In their retracted configurations, the membranes 90 and 92 form receptacles with the outer member 48 of the cover 30.

Figure 6A:
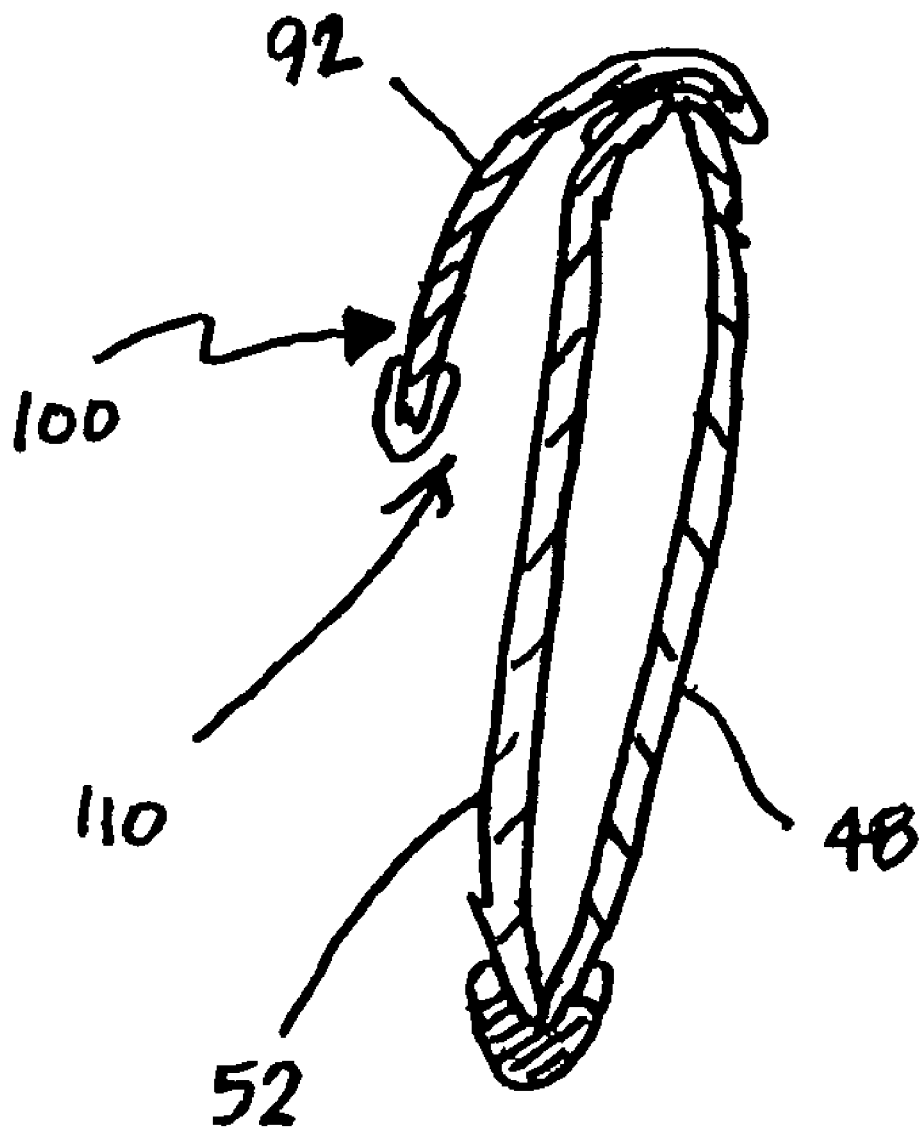
FIG. 6A is a cross-sectional front view of the ear warmer illustrated in FIG. 6 taken along line 6A—6A of FIG. 6.
Figure 7:
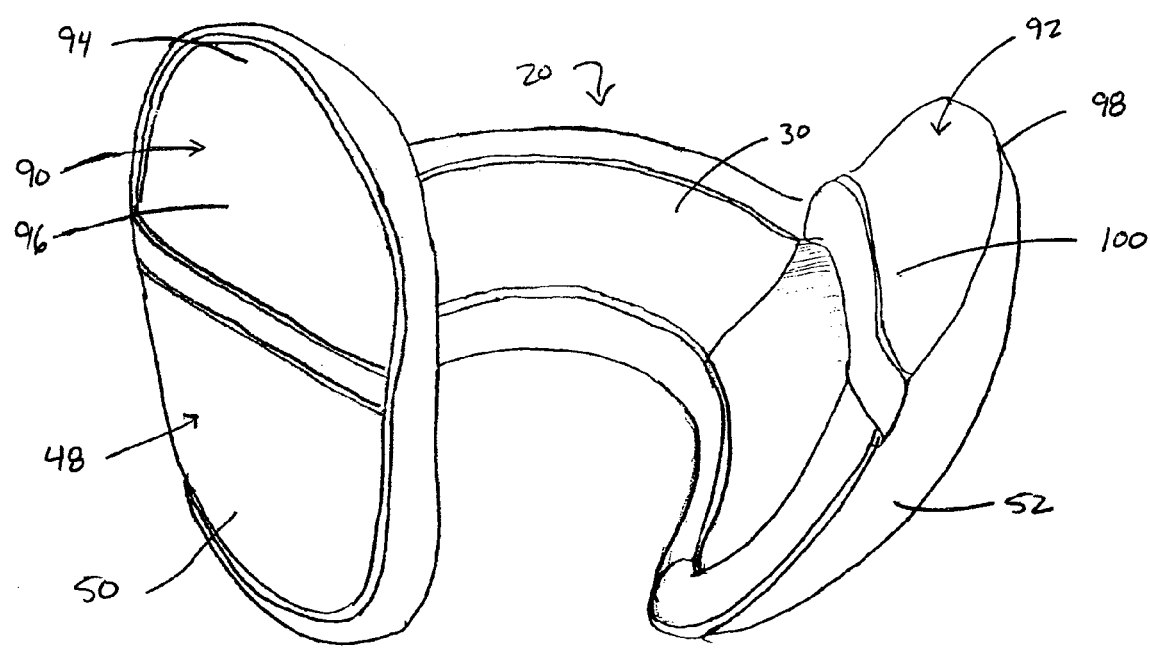
FIGS. 7–8 are perspective views of the ear warmer illustrated in FIG. 1 disposed in other configurations.

FIG. 6A illustrates a cross-sectional view of a portion of the ear warmer of FIG. 6. The ear portion 52 and the outer member 48 of the cover 30 and the membrane 92 are illustrated. The membrane 92 is shown in its deployed configuration. The membrane 92 and the ear portion 52 form a receptacle 110 therebetween. Membrane 90 and cover 30 form a substantially similar receptacle therebetween when the membrane 90 is in its deployed configuration (not illustrated in FIG. 6A).

The membranes 90 and 92 need not be in the same configuration. For example, in FIG. 7, the membrane 90 is disposed in a retracted configuration and the membrane 92 is disposed in a deployed configuration.

Figure 8:
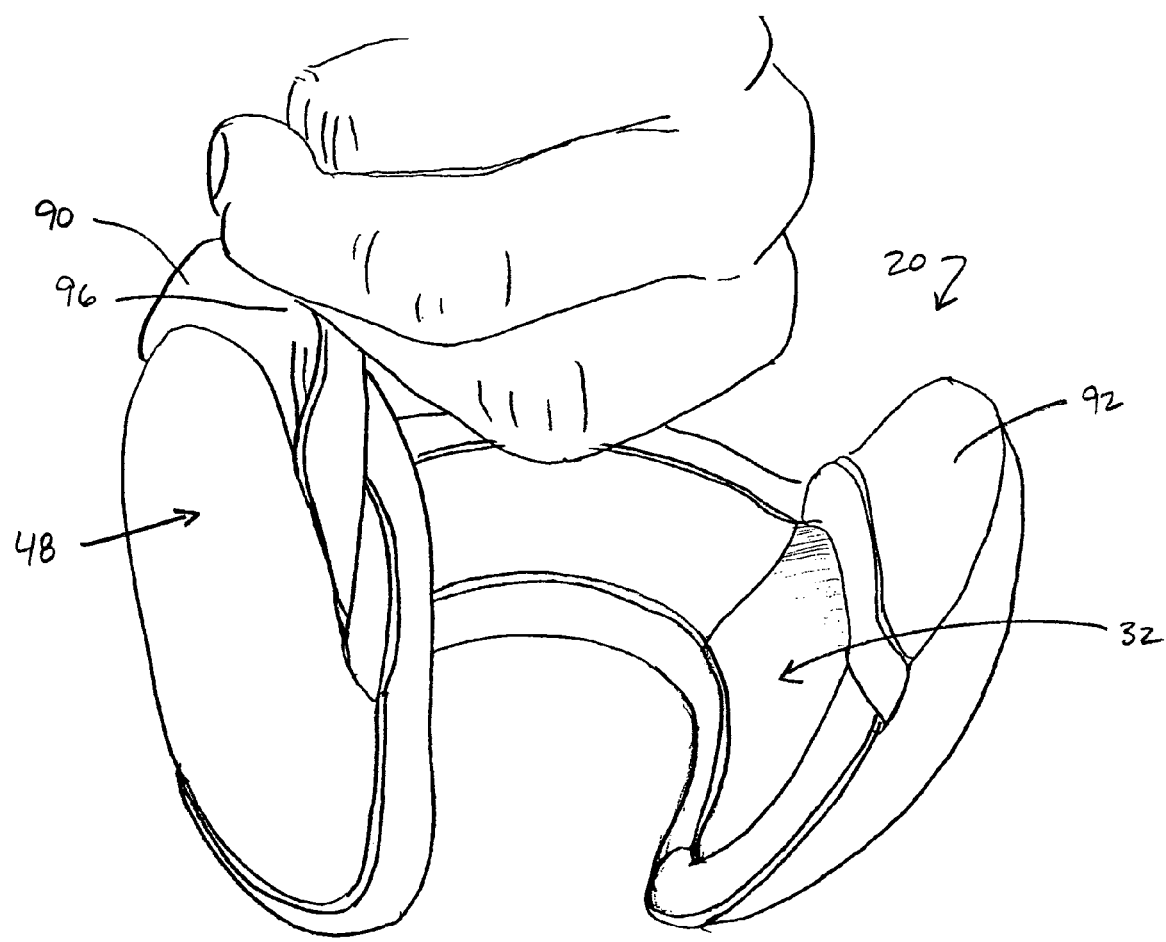

In FIG. 8, the membrane 92 is in a deployed configuration, and the membrane 90 is in a configuration between its retracted configuration and its deployed configuration. The membranes 90 and 92 are flipped or rotated about their connections with the cover 30 to reconfigure the membranes 90 and 92 between their retracted configurations and their deployed configurations.

For example, as illustrated in FIG. 8, to reconfigure the membrane 90 from a retracted configuration to a deployed configuration, a user grasps the membrane 90, such as by the distal portion 96, and rotates, flips, or otherwise moves the distal portion 96 of the membrane 90 from a position adjacent the outer member 48 of the cover 30 to a position adjacent the inner member 32 of the cover 30. Membrane 92 is similarly moved between its deployed and retracted configurations.

To reconfigure membrane 90 from its deployed configuration to its retracted configuration, the above steps are performed in reverse, i.e., the user grasps membrane 90 and rotates, flips, or otherwise moves the membrane 90 from a position adjacent the inner member 32 of the cover 30 to a position adjacent the outer member 48 of the cover 30. Membrane 92 can be similarly manipulated and positioned.

Figure 9:
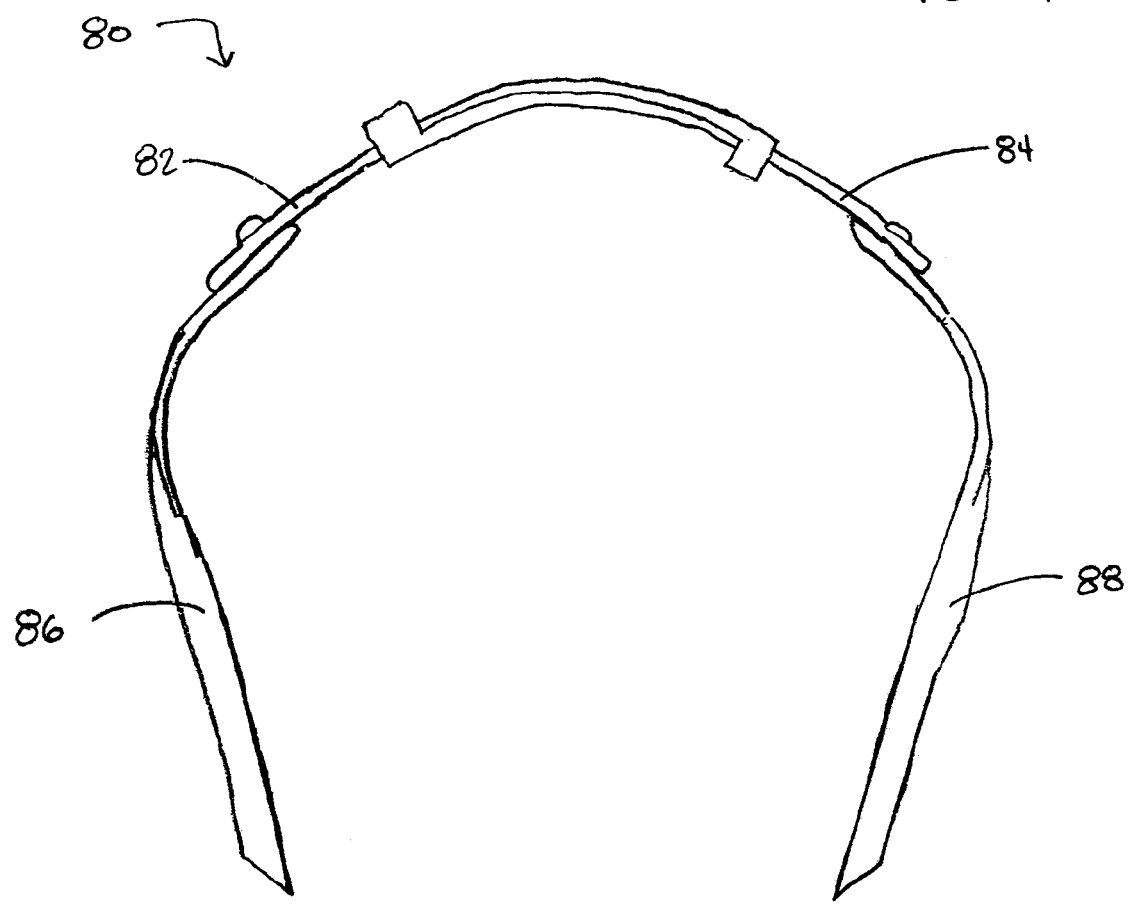
FIG. 9 is a top view of an example of an embodiment of a frame of the ear warmer illustrated in FIG. 1.

FIG. 9 illustrates a top view of an example of a frame that can be used with cover 30. In one embodiment, the frame 80 is configured to be disposed within the interior portion 56 of the cover 30. As illustrated in FIG. 4, at least a portion of the frame 80 is disposed within the interior portion 56 of the cover 30 between the heat-retaining member 46 and the ear pad 42.

In one embodiment, the frame 80 is a four piece frame and includes a first band member 82, a second band member 84, a first ear member 86, and a second ear member 88. In this embodiment, the frame 80 is adjustable in length because the first band member 82 is slidably coupled to the second band member 84. An example of an adjustable frame that includes a first band portion that is slidably coupled to a second band portion is disclosed in U.S. Pat. No. 5,835,609, the disclosure of which is incorporated herein by reference (see, e.g., FIGS. 28–38 and the associated written description in U.S. Pat. No. 5,835,609). In an alternative embodiment, each of the first ear member and the second ear member can be movably coupled to a band member to allow for adjustability of the frame. In an alternative embodiment, the frame can include a fixed length band member. Also, the ear members can be fixedly coupled to a band member.

Figure 10:
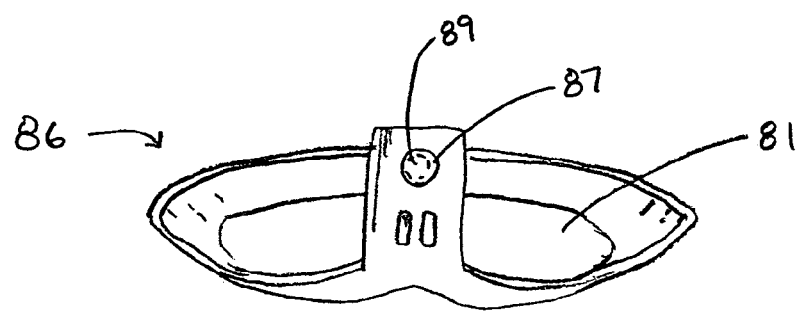
FIG. 10 is a rear perspective view of a portion of the frame illustrated in FIG. 9.

FIG. 10 illustrates the first ear member 86 of the frame 80. In the embodiment of FIG. 9, the second ear member 88 of the frame 80 is functionally and structurally similar to the first ear member 86. Therefore, only the first ear member 86 is illustrated in FIG. 10 and discussed in detail. In this embodiment, the first ear member 86 defines an opening 81. More specifically, the first ear member 86 has a frusto-conical shape that is conducive to being comfortably placed against a user's head. In other embodiments, the first ear member and the second ear member can have other shapes and configurations that can be placed against a user's head.

In the illustrated embodiment, the first ear member 86 includes a connection portion 87. The connection portion 87 includes a hole 89 that aligns with a similar hole (not illustrated) in first band member 82. A connection device such as a rivet, a screw, a pin, or any other known connection member extends though the hole of the first band member 82 and the hole 89 of the connection portion 87 to couple the first ear member 86 to the first band member 82. In an alternative embodiment, the connection portion of the first ear member 86 is an integral snap-fit connector that complementarily fits with an associated portion on the first band member 82.

The ear warmer 20 is configured to remain substantially in place on a head of a user when the ear warmer 20 is worn by the user. The frame 80 is configured to apply a compression force on the head of a user when the ear warmer 20 is worn by the user. Additionally, a receptacle formed by one of the membranes 90 and 92 and the cover 30 produces a friction force on a user's ear when the ear warmer 20 is worn by the user and the ear of the user is at least partially inserted into the receptacle. In other words, the user's ear acts as a mechanical stop so that the ear warmer 20 can hang on the user's ear. The compression force of the frame 80 and the friction force of the membrane/cover receptacle collectively secure the ear warmer 20 on the head of the user.

Figure 11:
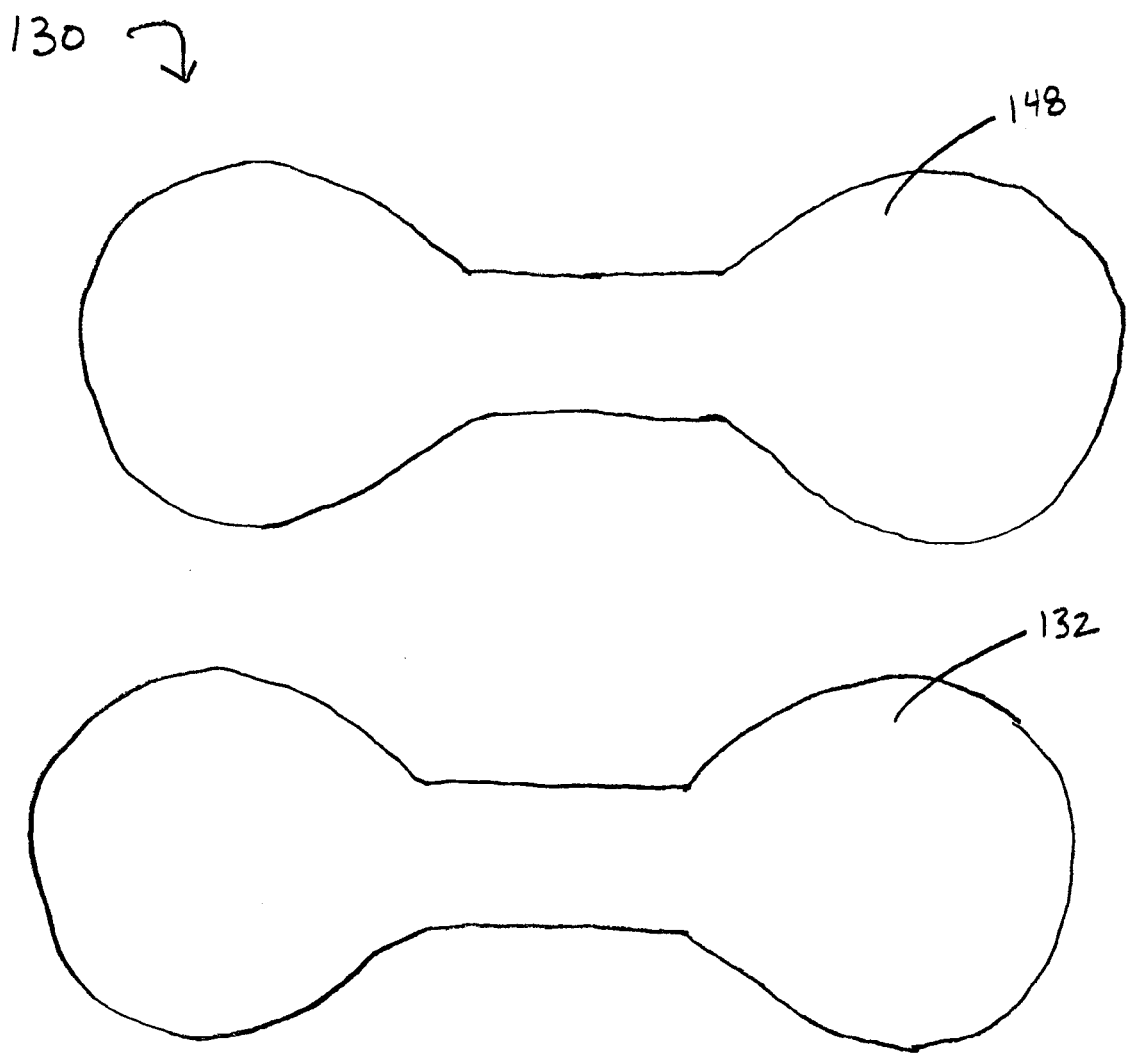
FIGS. 11–12 are top views of the members of covers according to other embodiments of the invention.

FIG. 11 illustrates an alternative embodiment of a cover that can be used in the ear warmer of the disclosed invention. The cover 130 is a two piece cover and includes an inner member 132 and an outer member 148. The inner member 132 is coupled to the outer member 148. The inner member 132 and the outer member 148 of the cover 130 define an interior region therebetween (not illustrated). An example of such a cover is disclosed in U.S. patent application Ser. No. 10/056,093, filed on Jan. 28, 2002, the disclosure of which is incorporated herein by reference.

In one embodiment, the inner member 132 is sewn along a portion of the perimeter of the inner member 132 to the outer member 148. In one embodiment, a binding is sewn to the inner member 132 and the outer member 148. In alternative embodiments, the inner member 132 is coupled to the outer member 148 via a tack, an adhesive, such as glue, or any other coupling mechanism or technique. Alternatively, the inner member 132 and the outer member 148 can be coupled together by a seam. In another embodiment, the inner member 132 is not coupled to the outer member 148 along a portion of the perimeter of the inner member 132; rather, another portion of the inner member 132 is coupled to the outer member 148. Membranes 90 and 92 can be coupled to the cover 30 as previously described.

Figure 12:
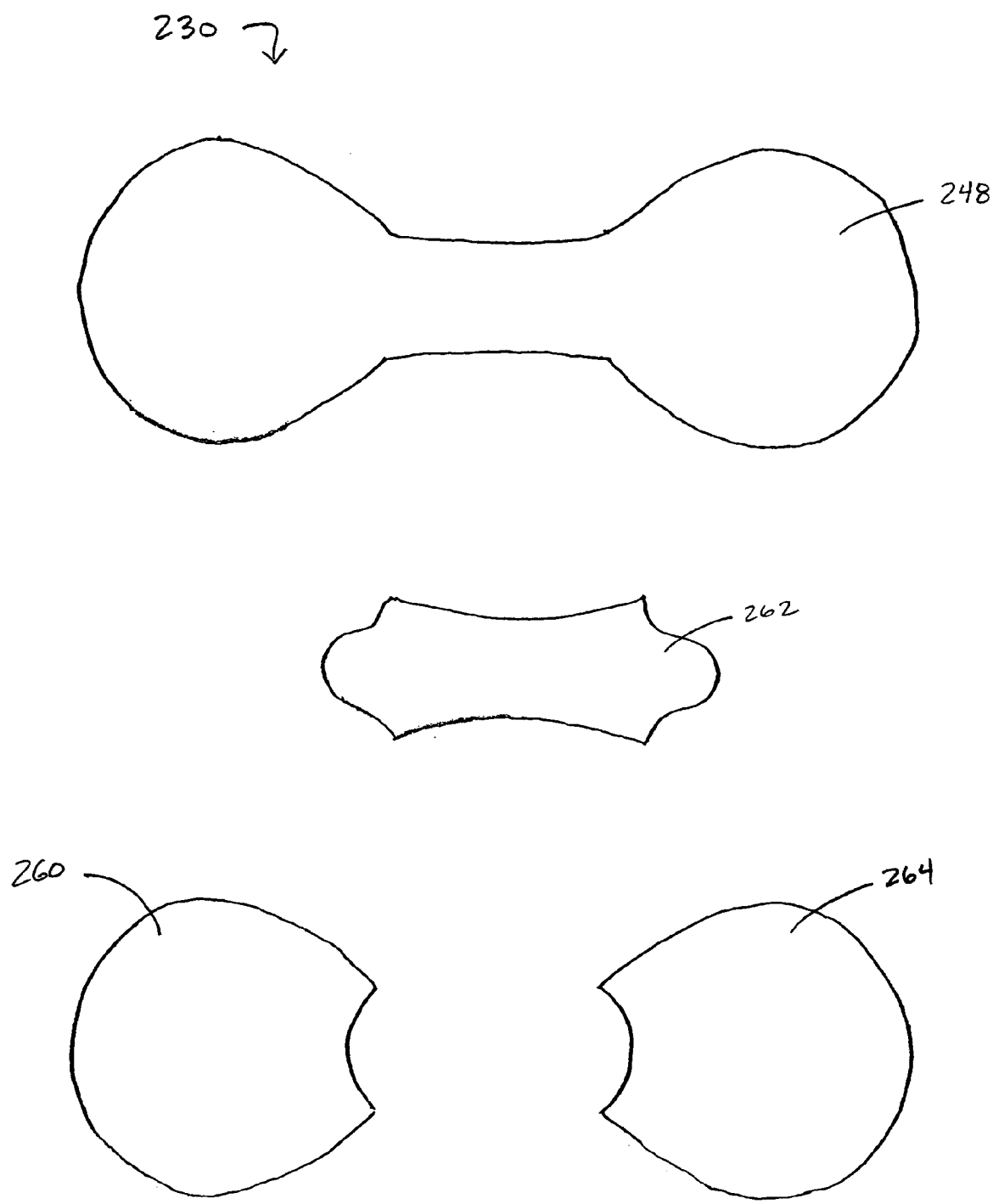

FIG. 12 illustrates a further alternative embodiment of a cover that can be used in the ear warmer of the disclosed invention. The cover 230 is a four piece cover and includes a first inner member 260, a second inner member 262, a third inner member 264, and an outer member 248. The inner members 260, 262, and 264 are coupled to the outer member 248. The inner members 260, 262, and 264 and the outer member 248 of the cover 230 collectively define an interior region therebetween (not illustrated). An example of such a cover is disclosed in U.S. patent application Ser. No. 10/056, 093, filed on Jan. 28, 2002, the disclosure of which is incorporated herein by reference.

In one embodiment, the inner members 260, 262, and 264 are sewn to the perimeter of the outer member 248. In alternative embodiments, the inner members 260, 262, and 264 are coupled to the outer member 248 via tacks, an adhesive, such as glue, or any other coupling mechanism or technique. Membranes 90 and 92 can be coupled to the cover 30 as previously described.

Figure 13:
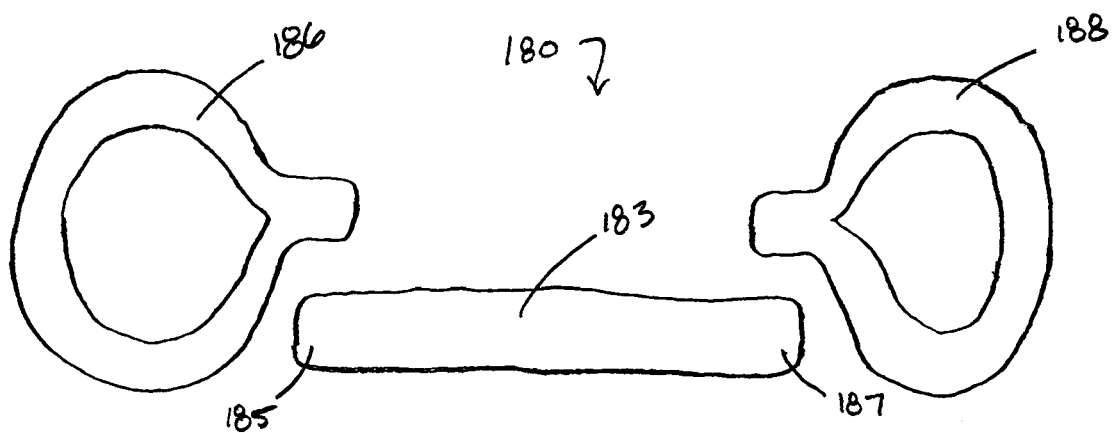
FIGS. 13–14 are top views of frames according to other embodiments of the invention.
Figure 14:
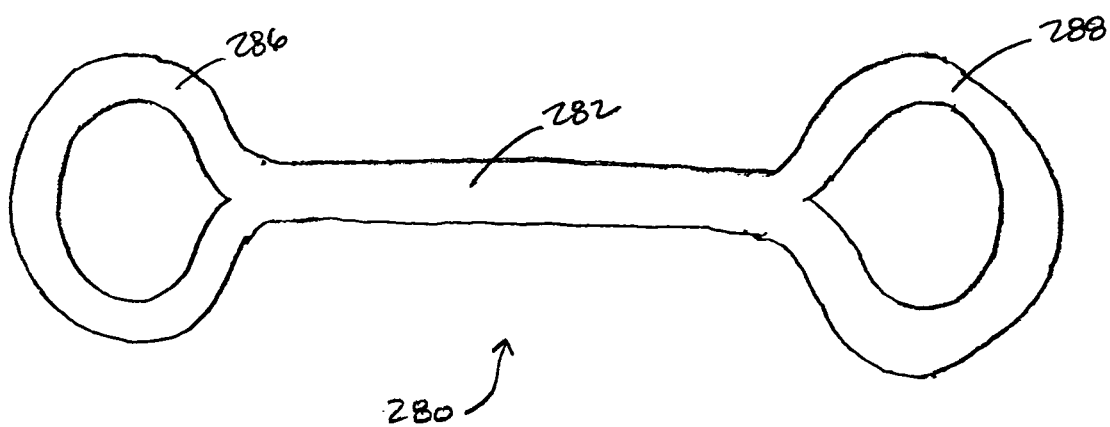

FIGS. 13 and 14 illustrate alternative embodiments of frames that may be used in the ear warmer of the present invention. As illustrated in FIG. 13, the frame 180 is a three piece frame. The frame 180 includes a band member 183, a first ear member 186, and a second ear member 188. In one embodiment, the first ear member 186 and the second ear member 188 each defines an opening.

The first ear member 186 is coupled to a first end 185 of the band member 183. Similarly, the second ear member 188 is coupled to a second end 187 of the band member 183. In one embodiment, each of the ear members 186 and 188 is coupled to the band member 183 via a rivet (not illustrated). In an alternative embodiment, each of the ear members 186 and 188 is coupled to the band member 183 via any another coupling mechanism or technique, such as a staple, an adhesive, or a button. In one embodiment, the first ear member 186, the second ear member 188, and the band member 183 are made of a plastic material. In alternative embodiments, the first ear member 186, the second ear member 188 and the band member 183 are made of another material, such as a metal.

Another example of a frame is illustrated in FIG. 14. Frame 280 is a single piece frame. The frame 280 includes a first ear portion 286, a second ear portion 288, and a band portion 282. Each of the ear portions 286 and 288 defines an opening. In one embodiment, the frame 280 is made of a plastic material. In an alternative embodiment, the frame is made of another material, such as a metal.

Figure 15:
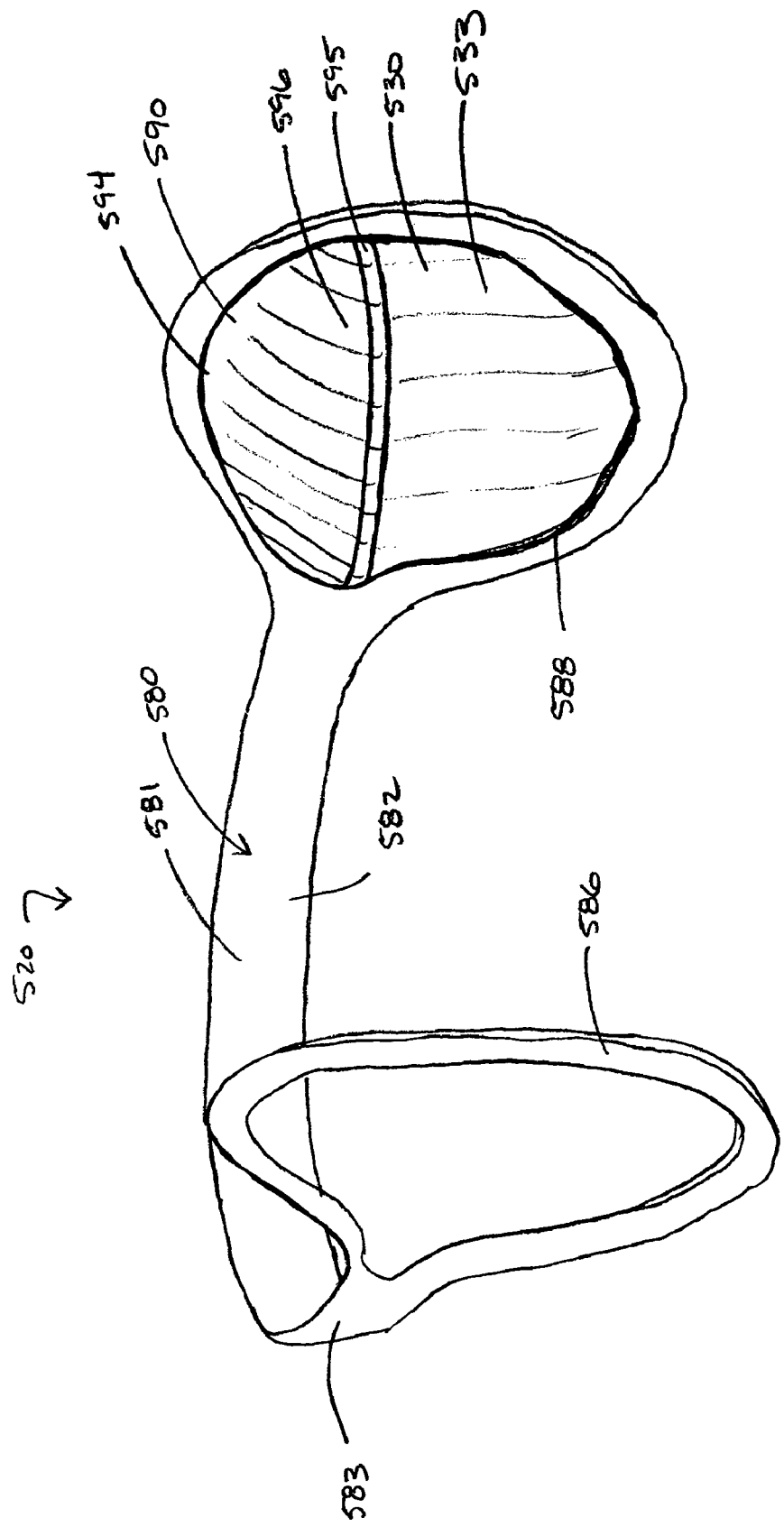
FIG. 15 is perspective view of an ear warmer according to another embodiment of the invention.

FIG. 15 illustrates an alternative embodiment of the ear warmer in according to the invention. The ear warmer 520 includes two covers 530 (only one is illustrated), two membranes 590 (only one is illustrated), and a frame 580.

In the illustrated embodiment, the frame 580 is a one piece frame and has a first ear portion 586, a second ear portion 588, and a band portion 582. In an alternative embodiment, the frame 580 can be made of multiple components that are fixedly or removably coupled to each other. The frame 580 includes an inner side 581 (the side of the frame that is disposed adjacent a user's head when the ear warmer is worn by the user) and an outer side 583 (the side of the frame that is disposed not in contact with a user's head when the ear warmer is worn by the user).

The covers 530 are substantially similar to each other in function and structure. Therefore, only one cover will be discussed in detail. The cover 530 is a single layer of material that is configured to cover one side of the ear portion 588 of the frame 580. In an alternative embodiment, the cover 530 can cover at least a portion of more than one side of the ear portion 588 of the frame 580. In another alternative embodiment, the cover 530 can cover one side of the ear portion and at least a portion of the band portion.

In this embodiment, the cover 530 is coupled to the inner side 581 of the frame 580 via a RF (radio frequency) weld or an ultrasonic weld. It is not necessary, however, that the cover be coupled to the inner side 581 of the frame 580 via a weld. In alternative embodiments, the cover is coupled, via any known coupling method, to any other portion of the frame. For example, the cover may be coupled to the outer side of the frame via any coupling technique, such as a weld or an adhesive, such as glue.

In this embodiment, at least a portion of the frame 580 of the ear warmer 520 is exposed (meaning that at least a portion of the frame is not covered by the cover 530). In this embodiment, the band portion 582 of the frame 580 and the outer sides of the ear portions 586 and 588 are not covered by the cover 530. In alternative embodiments, more or less of the frame 580 is covered by the cover 530.

The membranes 590 are substantially similar to each other in function and structure. Therefore, only one membrane 590 will be discussed in detail. The membrane 590 is flexible and is coupled to an inner side 533 (the side of the cover 530 that is disposed adjacent a user's head when the ear warmer is worn by the user) of the cover 530. The membrane 590 has a proximal portion 594 (the portion of the membrane 590 proximal to the coupling of the membrane 590 and the cover 530) and a distal portion 596 (the portion of the membrane 590 distal from the coupling of the membrane 590 and the cover 530).

The membrane 590 has a deployed configuration and a retracted configuration. When the membrane 590 is in its deployed configuration, a distal portion 596 of the membrane is disposed adjacent an inner side 533 of the cover 530 (see FIG. 15). The membrane 590 and the inner side 533 of the cover 580 form a receptacle that is configured to receive at least a portion of an ear of a user when the ear warmer 520 is worn by the user. When the membrane 590 is in its retracted configuration, the distal portion 596 is disposed adjacent an outer side (the side of the cover opposite the inner side) (not illustrated) of the cover 530.

In one embodiment, the membrane 590 is sewn to the cover 530. Additionally, in one embodiment, the membrane 590 includes a binding 595 coupled to an edge of the membrane 590. It is not necessary, however, that the membrane 590 includes a binding 595. Additionally, it is not necessary that the membrane 590 be sewn to the cover 530. In alternative embodiments, the membrane 590 is coupled to any portion of the cover 530 via any known coupling method. In further alternative embodiments, the membrane 590 is coupled to a portion of the frame 580, such as the first ear portion 588 of the frame 580, via any known coupling method.

In alternative embodiments, the membranes can have any shape or configuration. The configuration of the proximal portion of a membrane does not have to be substantially the same as the perimeter of a part of the cover.

In alternative embodiments, the membranes can be coupled at any location on the ear warmer that allow a user to insert the user's ears into receptacles formed by the membranes on the ear warmer.

In an alternative embodiment, the ear warmer includes two ear portions and a membrane coupled to each of the ear portions. The ear warmer also includes a cover that is configured to extend around the back of a user's head. The cover is also configured to cover at least a portion of the ear portion. An ear warmer with such a cover is described in co-pending patent application entitled "Ear Warmer Having an External Frame," application Ser. No. 10/638,476, filed the same day, the disclosure of which is herein incorporated by reference.

While the invention has been described in detail and with references to specific embodiments thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

What is claimed is:

1. An ear warmer, comprising:
a cover having an outer member and an inner member, the outer member and the inner member defining an interior region therebetween;
a frame, at least a portion of the frame being disposed in the interior region defined by the outer member and the inner member;
a first membrane coupled to the cover, the first membrane and the inner member of the cover forming a first receptacle configured to receive at least a portion of an ear of a user between the membrane and the cover; and
a second membrane coupled to the cover, the second membrane and the inner member of the cover forming a second receptacle configured to receive at least a portion of another ear of the user.

2. The ear warmer of claim 1, wherein the first membrane has a movable portion and a fixed portion, the first membrane has a deployed configuration and a retracted configuration, the movable portion of the first membrane being disposed adjacent the inner member when the first membrane is in its deployed configuration, at least a portion of the movable portion of the first membrane being disposed adjacent the outer member when the first membrane is in its retracted configuration.

3. The ear warmer of claim 1, wherein the cover has a first ear portion, a second ear portion, and a middle portion extending between the first ear portion and the second ear portion, and the first membrane is coupled to a portion of one of the first ear portion and the second ear portion.

4. The ear warmer of claim 1, wherein the cover has an ear portion, the ear portion of the cover has a perimeter, the first membrane is coupled to the ear portion along a portion of the perimeter of the ear portion, the portion of the perimeter is less than the entire perimeter of the ear portion.

5. The ear warmer of claim 1, wherein the frame is configured to extend around a back of a head of the user.

6. The ear warmer of claim 1, wherein the first membrane is coupled to the outer member of the cover.

7. The ear warmer of claim 1, wherein the first membrane is coupled to the inner member of the cover.

8. The ear warmer of claim 1, wherein a portion of the first membrane is disposed between the inner member of the cover and the outer member of the cover.

9. The ear warmer of claim 1, wherein the frame and the first membrane are configured to collectively secure the ear warmer to a head of the user.

10. An ear warmer, comprising:
a frame having a first ear portion, a second ear portion, and a band extending between the first ear portion and the second ear portion;
a cover member coupled to the frame such that at least a portion of the first ear portion is covered by the cover member, the cover member including a first membrane portion and a second membrane portion, the first ear portion including an inner side and an outer side, the first membrane portion being disposed proximate to the inner side of the first ear portion and the second membrane portion being disposed proximate to the outer side of the second ear portion; and
a membrane coupled to at least one of the cover member and the frame, the membrane and the cover member forming a receptacle configured to receive at least a portion of an ear of a user between the membrane and the cover member, and the first membrane portion, the second membrane portion and the membrane are coupled together using a binding.

11. The ear warmer of claim 10, wherein the membrane has a movable portion and a fixed portion, the membrane has a deployed configuration and a retracted configuration, the cover member having an inner surface and an outer surface opposite the inner surface, the movable portion of the membrane is disposed adjacent the inner surface of the cover member when the membrane is in its deployed configuration, the movable portion of the membrane is disposed adjacent the outer surface of the cover member when the membrane is in its retracted configuration, the fixed portion of the membrane being fixedly coupled to the at least one of the cover member and the frame.

12. The ear warmer of claim 10, wherein the the cover member is configured to cover a portion of the first side of the first ear portion less than an entirety of one of the sides of the first ear portion.

13. The ear warmer of claim 10, the cover member being a first cover member, the membrane being a first membrane, the receptacle being a first receptacle, the ear warmer further comprising:
a second cover member configured to cover at least a portion of the second ear portion; and
a second membrane coupled to at least one of the second cover member and the frame, the second membrane and the second cover member forming a second receptacle configured to receive at least a portion of another ear of the user.

14. The ear warmer of claim 10, wherein the frame is configured to extend around a back of a head of the user.

15. The ear warmer of claim 10, wherein a compression force applied by the frame and a friction force by the membrane collectively are configured to substantially secure the ear warmer to a head of the user.

16. The ear warmer of claim 10, wherein the membrane having a first position and a second position, the distal end of the membrane being proximate to the first membrane portion in its first position and proximate to the second membrane portion in its second position.

17. The ear warmer of claim 16, wherein the first membrane portion has a perimeter portion, the second membrane portion has its own perimeter portion, the first membrane portion being coupled to the second membrane portion along a portion of their perimeter portions, the membrane being coupled along a portion of the perimeter of the first membrane portion.

18. The ear warmer of claim 10, wherein the frame has a deployed configuration and a collapsed configuration, the membrane being configured to be disposed in a first position and in a second position, the membrane being selectively disposable in one of the first position and the second position when the frame is in its deployed configuration.

19. The ear warmer of claim 18, wherein the distal end of the membrane is configured to be disposed proximate to the outer side of the first ear portion in its first position and the membrane is configured to be disposed proximate to the inner side of the first ear portion in its second position.

20. An ear warmer, comprising:
a frame;
a cover having an inner member and an outer member, the cover covering a portion of the frame less than the entirety of the frame, the cover including a perimeter;
a first membrane coupled along a portion of the perimeter of the cover, the first membrane having a first configuration and a second configuration, a portion of the first membrane being disposed adjacent the inner member of the cover when the first membrane is in its first configuration, the portion of the first membrane being disposed adjacent the outer member of the cover when the first membrane is in its second configuration and
a second membrane coupled along a portion of the perimeter of the cover, the second membrane having its own first configuration and its own second configuration, a portion of the second membrane being disposed adjacent the inner member of the cover when the second membrane is in its first configuration, the portion of the second membrane being disposed adjacent the outer member of the cover when the second membrane is in its second configuration.

21. The ear warmer of claim 20, wherein the first membrane and the inner member of the cover forming a first receptacle when the first membrane is in its first configuration, the receptacle being configured to receive at least a portion of an ear of a user when the first membrane is in its first configuration, the second membrane and the inner member of the cover forming a second receptacle when the second membrane is in its first configuration, the receptacle being configured to receive at least a portion of another ear of the user when the second membrane is in its first configuration.

22. The ear warmer of claim 20, wherein the frame is configured to extend around a back of a head of a user.

23. The ear warmer of claim 20, wherein a portion of the inner member, a portion of the outer member and a portion of the first membrane are coupled together proximate to the perimeter.

24. The ear warmer of claim 23, wherein the inner member has an ear portion with a perimeter, and the first membrane has an edge portion, the edge portion of the first membrane being coupled to the ear portion of the inner member proximate the perimeter of the ear portion.

25. An ear warmer, comprising:
a frame;
a cover having an inner side and an outer side, the cover covering a portion of the frame less than the entirety of the frame, the cover including a perimeter;
a first membrane coupled along a portion of the perimeter of the cover, the first membrane having a first configuration and a second configuration, a portion of the first membrane being disposed adjacent the inner side of the cover when the first membrane is in its first configuration, the portion of the first membrane being disposed adjacent the outer side of the cover when the first membrane is in its second configuration and
a second membrane coupled along a portion of the perimeter of the cover, the second membrane having its own first configuration and its own second configuration, a portion of the second membrane being disposed adjacent the inner side of the cover when the second membrane is in its first configuration, the portion of the second membrane being disposed adjacent the outer side of the cover when the second membrane is in its second configuration.

26. A method of manufacturing an ear warmer, having an inner member, an outer member, and a membrane, the method comprising:
disposing the membrane between the inner member and, the outer member, the inner member and the outer member being coupled together to define an interior region therebetween, the interior region being configured to receive a frame, the membrane being configured to be disposed proximate to an outer surface of one of the inner member and the outer member outside of the interior region such that the membrane and the outer surface form a receptacle therebetween, the receptacle being configured to receive a portion of a user's ear between the membrane and the outer surface; and
coupling the group consisting of the inner member, the outer member, and the membrane.

* * * * *